United States Patent [19]

McCarthy

[11] Patent Number: 4,603,030
[45] Date of Patent: Jul. 29, 1986

[54] SCENT-EMITTING SYSTEMS

[76] Inventor: Robert E. McCarthy, 18333 Lahey St., Northridge, Calif. 91326

[21] Appl. No.: 652,865

[22] Filed: Sep. 20, 1984

[51] Int. Cl.4 ............................................... A61L 9/04
[52] U.S. Cl. ......................................... 422/4; 239/60; 261/26; 261/30; 261/104; 261/DIG. 17; 352/85; 422/124
[58] Field of Search ................. 261/18 R, 26, 30, 104, 261/107, 109, DIG. 17, DIG. 65; 422/4, 122–124; 55/231; 239/48, 52, 60; 352/85

[56] References Cited

U.S. PATENT DOCUMENTS

| | | | |
|---|---|---|---|
| 1,081,523 | 12/1913 | Berardi | 261/30 |
| 2,562,959 | 8/1951 | Stern | 352/85 |
| 2,562,960 | 8/1951 | Stern | 352/85 |
| 2,813,452 | 11/1957 | Laube | 422/4 X |
| 2,905,049 | 9/1959 | Laube | 422/4 X |
| 3,014,353 | 12/1961 | Scully et al. | 239/60 X |
| 3,795,438 | 3/1974 | Westenholz et al. | 352/85 |
| 3,796,541 | 3/1974 | Gentil | 261/104 X |
| 3,908,906 | 9/1975 | Crowle et al. | 239/60 X |
| 4,159,672 | 7/1979 | Garguilo et al. | 261/104 X |
| 4,229,415 | 10/1980 | Bryson | 422/124 X |

Primary Examiner—Richard L. Chiesa
Attorney, Agent, or Firm—Kendrick, Netter & Bennett

[57] ABSTRACT

A system for emitting, in sequence, a plurality of different scents includes a plurality of holders for scent-bearing chips; a mechanism for propelling these scents from a system; a mechanism for conveying, selectively, any desired scent holder into operative relation with the propelling mechanism; and a mechanism for actuating the propelling mechanism to propel scent from any desired scent holder in response to a programmed, predetermined sequence of scents of predetermined duration.

13 Claims, 28 Drawing Figures

U.S. Patent  Jul. 29, 1986  Sheet 1 of 13  4,603,030
FIG. 1.
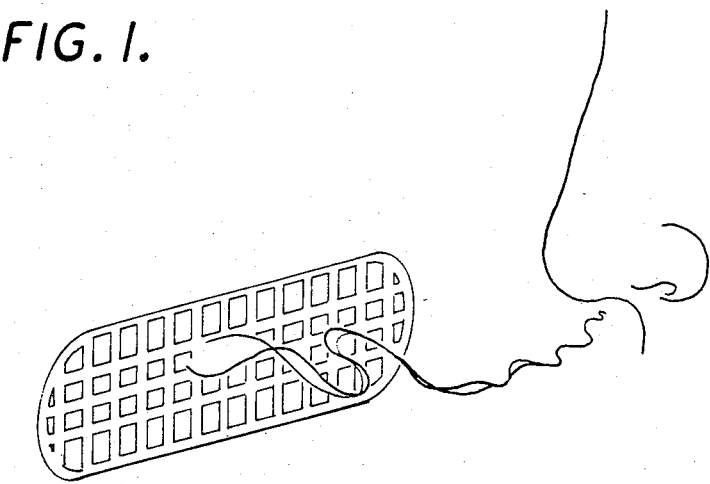
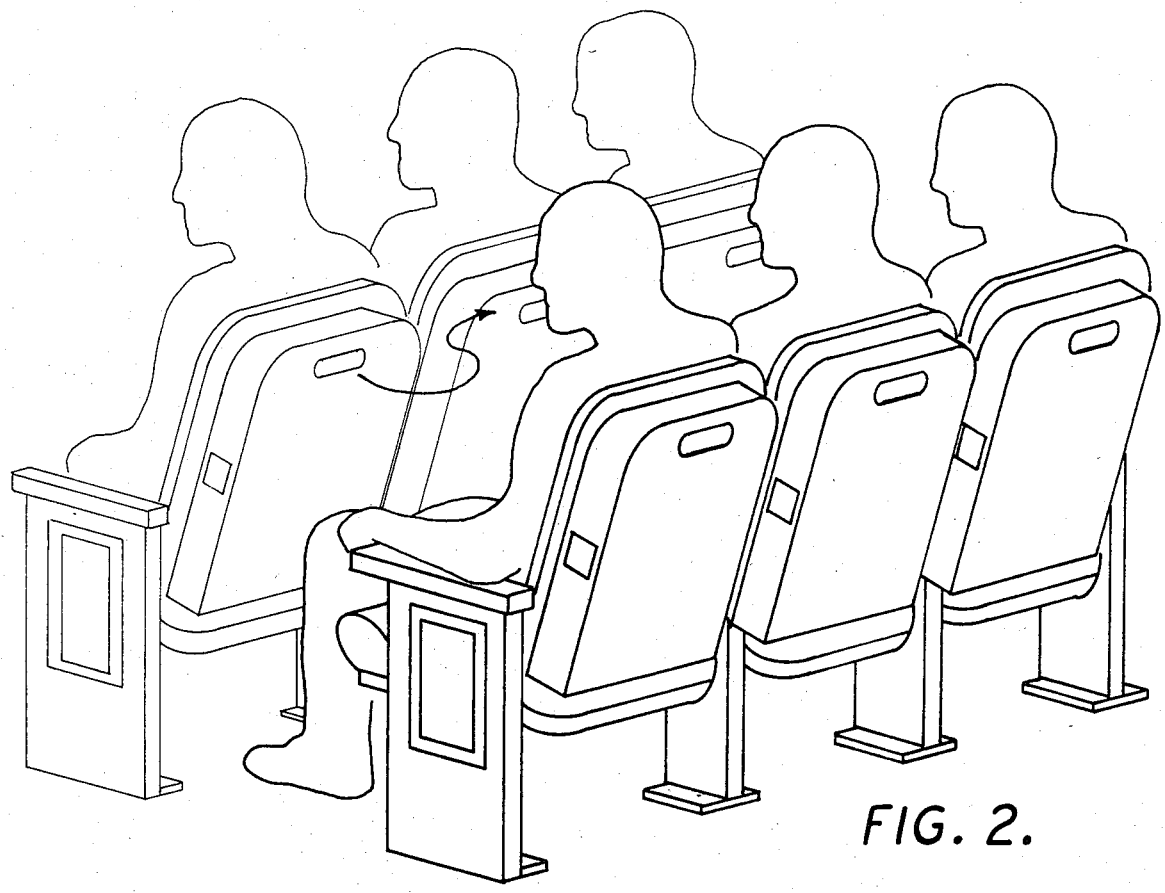
FIG. 2.

FIG. 4.
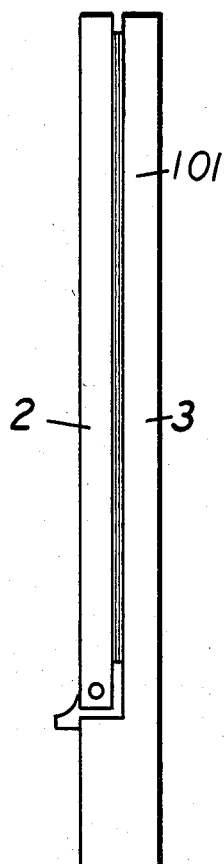
FIG. 4A
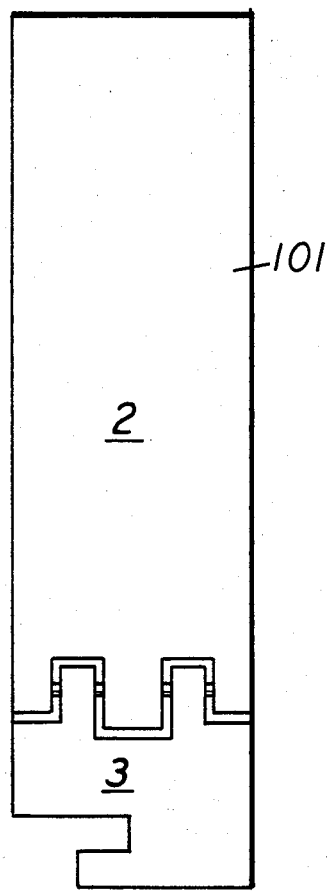
FIG. 4B
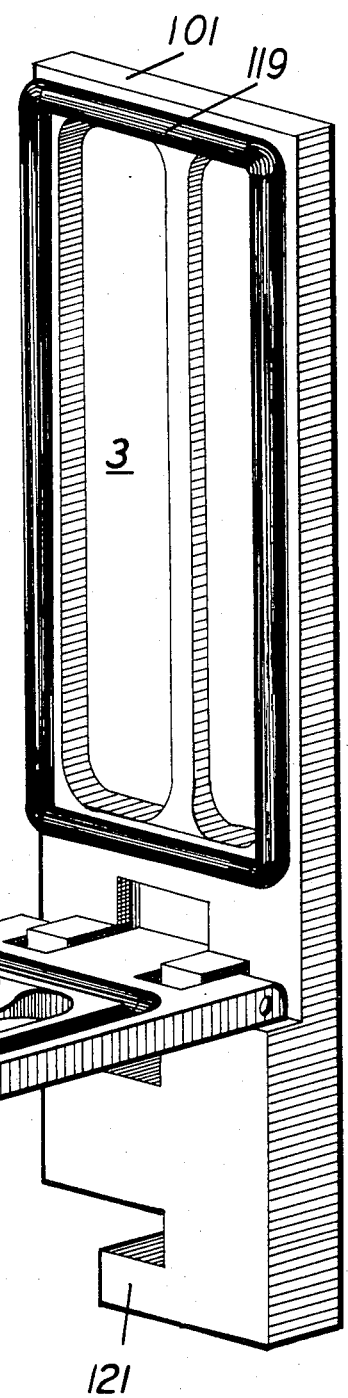
FIG. 4C

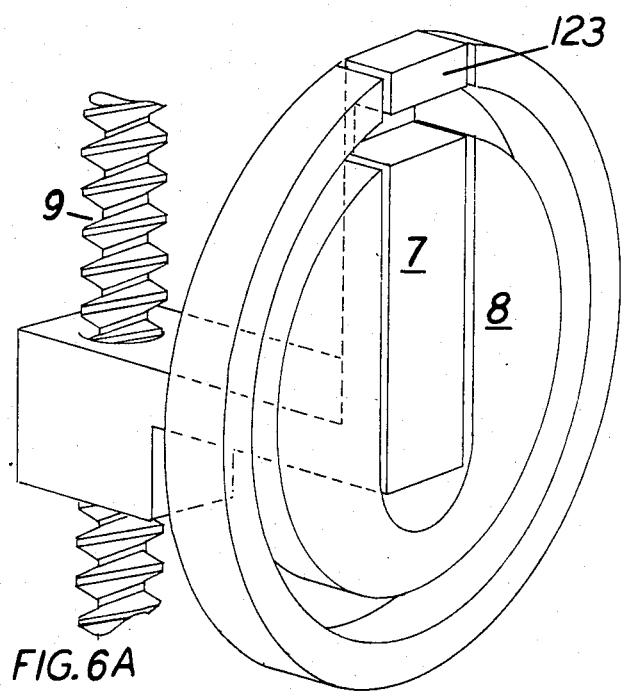
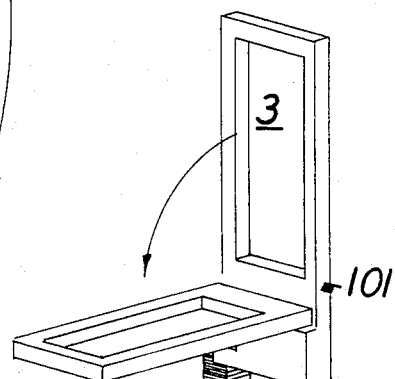
FIG. 6.
FIG. 6A.
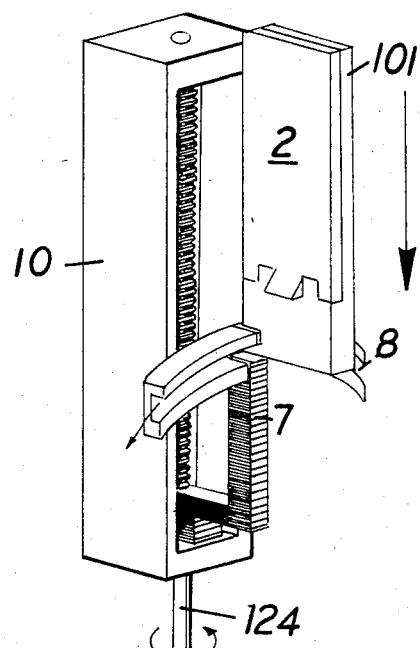
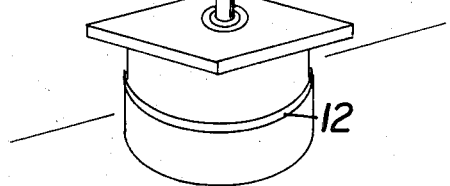
FIG. 6B.
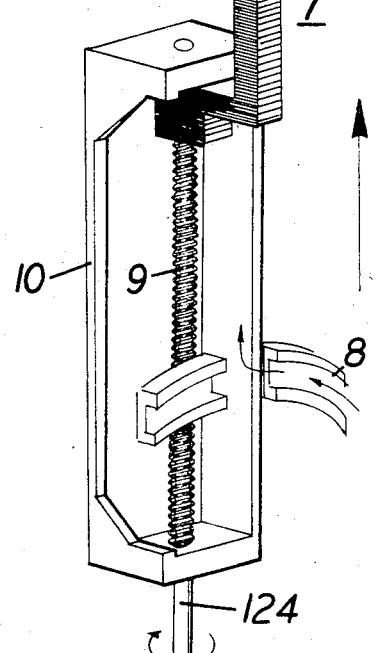
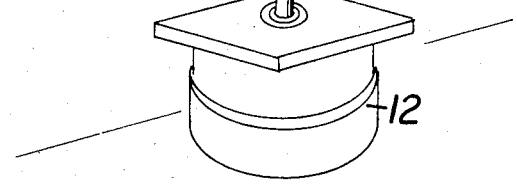
FIG. 6C.

FIG. 9.
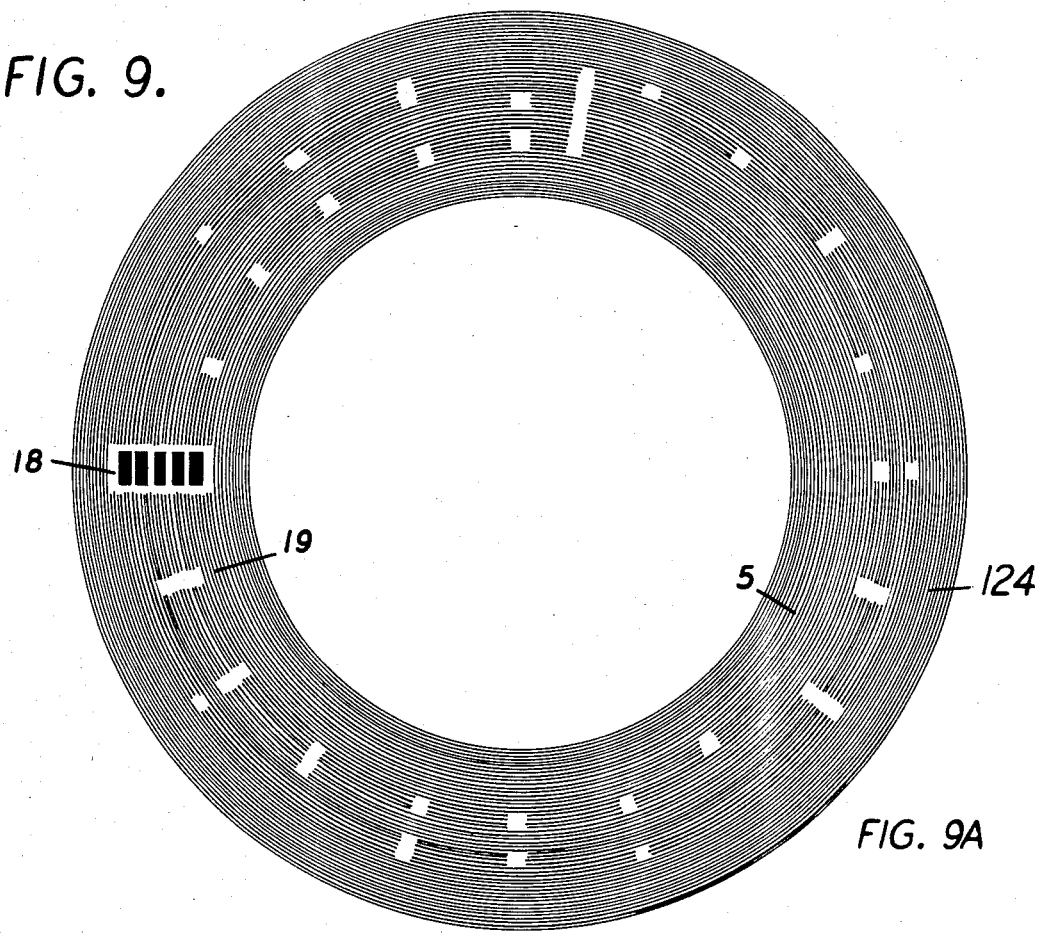
FIG. 9A
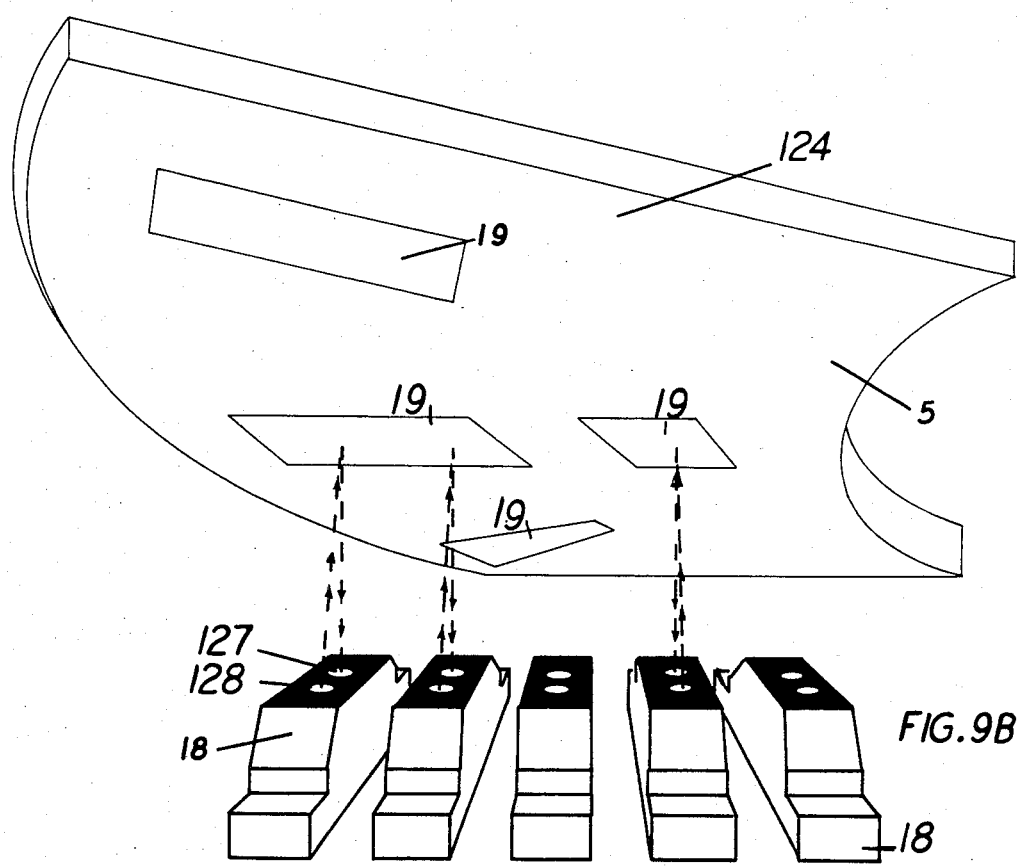
FIG. 9B

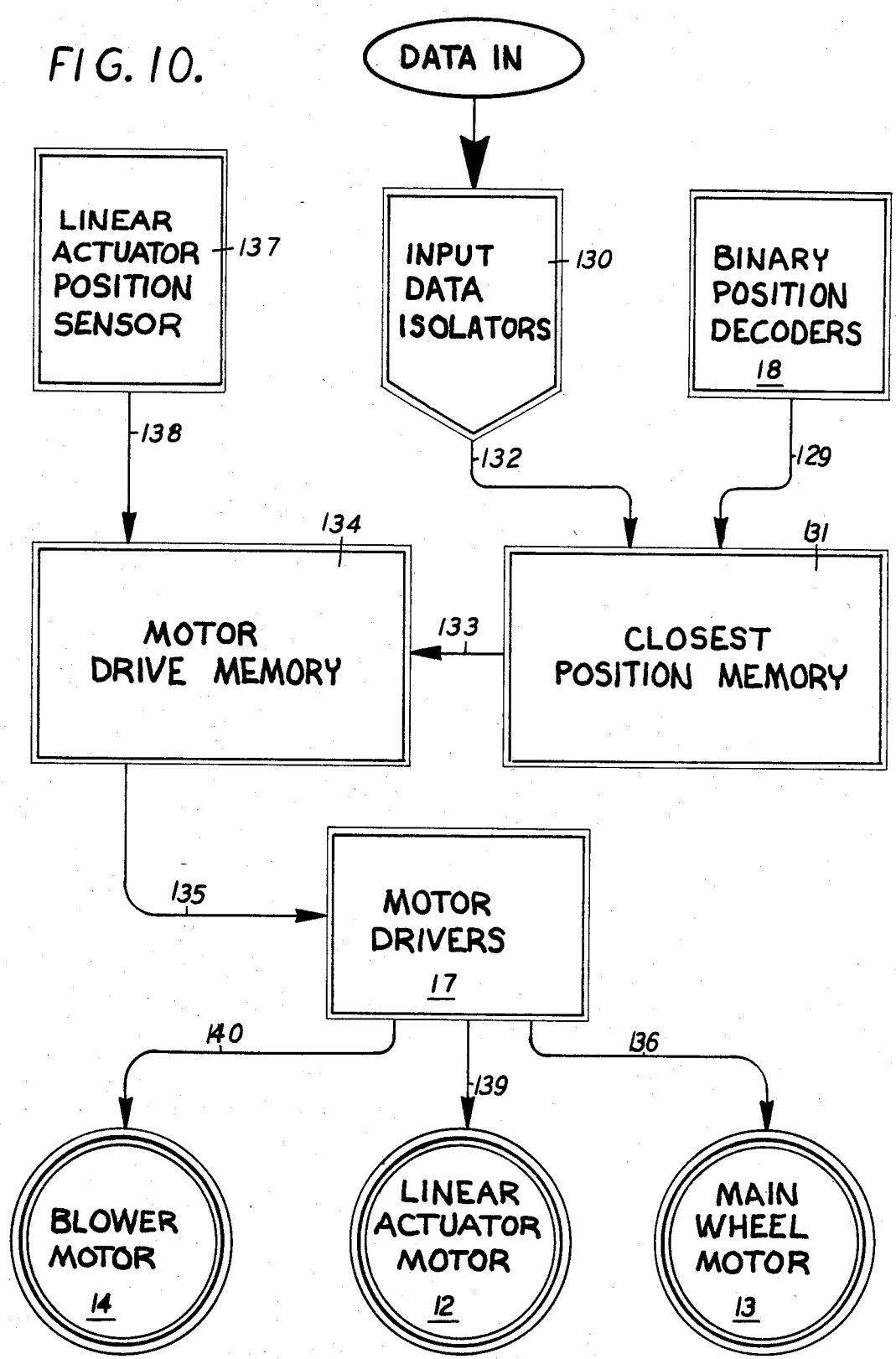

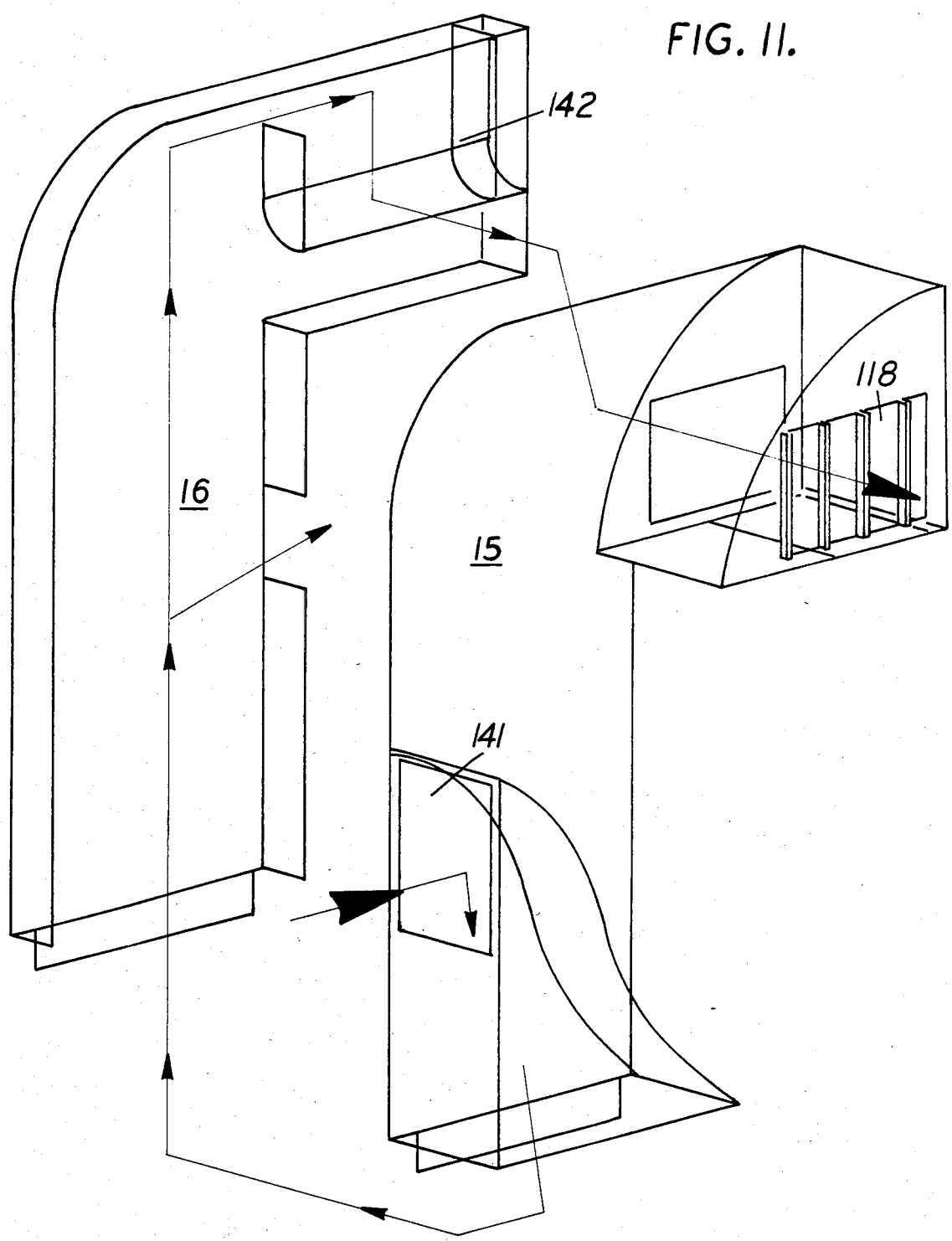

SCENT-EMITTING SYSTEMS

This invention relates to a system for emitting, in sequence, a plurality of different scents. In preferred embodiments, this scent-emitting system can deliver, in rapid succession, as many as 10, 20, or 30 different scents within as short a time as 30 minutes. The system can also deliver the same scent more than once in any sequence of two or more different scents.

The invention provides a system for selectively emitting, in sequence, one or more of a plurality of different scents comprising: a plurality of means for holding scent-bearing means; means for propelling these scents from the system; means for selectively conveying any desired holding means into operative relation with the propelling means; and means for actuating the propelling means to propel scent from the desired holding means.

In preferred embodiments, each of the holding means is an openable, closable shell that opens to release scent from the shell when the shell is in operative relation with the propelling means. In these embodiments, the scent-bearing means may be a removable insert such as a scent-impregnated plastic insert. Preferably, the insert has an irregular surface to increase its scent-emitting area.

The scent-emitting system also comprises means for conveying any desired means for holding scent-bearing means into operative relation with the scent-propelling means of the system. In preferred embodiments, the holding means are carried by rotatable, wheel-like means. Such rotatable means can carry a plurality of holding means numbering 5, 10, 20, 30, or more. In preferred embodiment, then, the system can have one propelling means and a plurality of means for holding scent-bearing means mounted on a rotatable means for carrying any desired holding means to a position from which the holding means can be placed into operative relation with the propelling means.

In preferred embodiments, the rotatable means that carries the plurality of means for holding scent-bearing means comprises a wheel-like array of means for closing each holding means, and for confining within each such holding means, scent emitted from the scent-bearing means within the holding means. In preferred embodiments, the rotatable, wheel-like means comprises two parallel support members and joined to one another by the means for closing the means for holding scent-bearing means. Either support member can include means for rotating the wheel-like rotatable means, and means for detecting the position of the rotatable means relative to the scent-propelling means of the system.

By turning the rotatable means, any desired means for holding scent-bearing means can be moved into engagement with means for positioning the holding means in operative relation with the propelling means of the system. This positioning means includes means for disengaging the scent-holding means from the means for closing the scent-holding means; for placing the disengaged scent-holding means in operative relation with the disengaged scent-propelling means of the system; and for thereafter opening the disengaged scent-holding means to release scent therefrom. This same positioning means also withdraws the scent-holding means from operative relation with the propelling means, and returns the scent holding means to engagement with the means for closing the scent-holding means.

The scent-propelling means of the system comprises means for withdrawing a gas such as air from a source, and means for directing the gas across scent-holding means when the scent-holding means is open to emit scent confined within the scent-holding means. In preferred embodiments, the scent-propelling means includes a blower fan and ductwork. The entrance to the ductwork is positioned near the fan or other means for drawing air into the system. The ductwork channels and directs gas flow to exit means. From the exit of the propelling means, the gas passes over the scent-bearing means exposed to such gas flow by the opening of means for holding the scent-bearing means. Gas flow across the scent-bearing means entrains scent emerging from the exit of the propelling means, and carries the entrained scent toward a system user.

The system also includes means for inputting a signal representing a desired scent and the time for emitting the desired scent; means for generating a signal representing the position of the rotatable means carrying the scent-holding means in relation to the propelling means; means for determining whether rotation of the rotatable means is necessary to convey a desired scent-holding means into operative relation with the scent-propelling means of the system; means for generating a signal representing the necessary distance and direction of rotation of the rotatable means to engage the desired scent-holding means with means for positioning this holding means in operative relation with the scent-propelling means; means for generating a signal to place the desired scent-holding means into operative relation with the propelling means and to open the scent-holding means to emit the desired scent; and means for actuating a blower motor or other means for propelling a gas such as air across the exposed scent-bearing means to entrain and carry the desired scent out of the system toward a potential user.

The invention can better be understood by reference to the drawings, in which:

FIG. 1 shows generally the emission of a desired scent from the scent-emitting system, and conveyance of the desired scent toward the nose of the system user;

FIG. 2 shows generally the attachment of one embodiment of the scent-emitting system of this invention to the backs of chairs in a theater for use by individuals seated behind such chairs;

FIGS. 4A and 4B show, respectively, exploded edge elevation and side elevation views of a preferred embodiment of the scent-holding means, in closed position;

FIG. 4C shows a perspective view of the same scent-holding means as FIGS. 4A and 4B, but here in the open position;

FIG. 6A is an exploded view showing certain parts of the means for positioning the scent-holding means in operative relation with the scent-propelling means of the system embodiment shown in FIG. 3;

Figure 3:
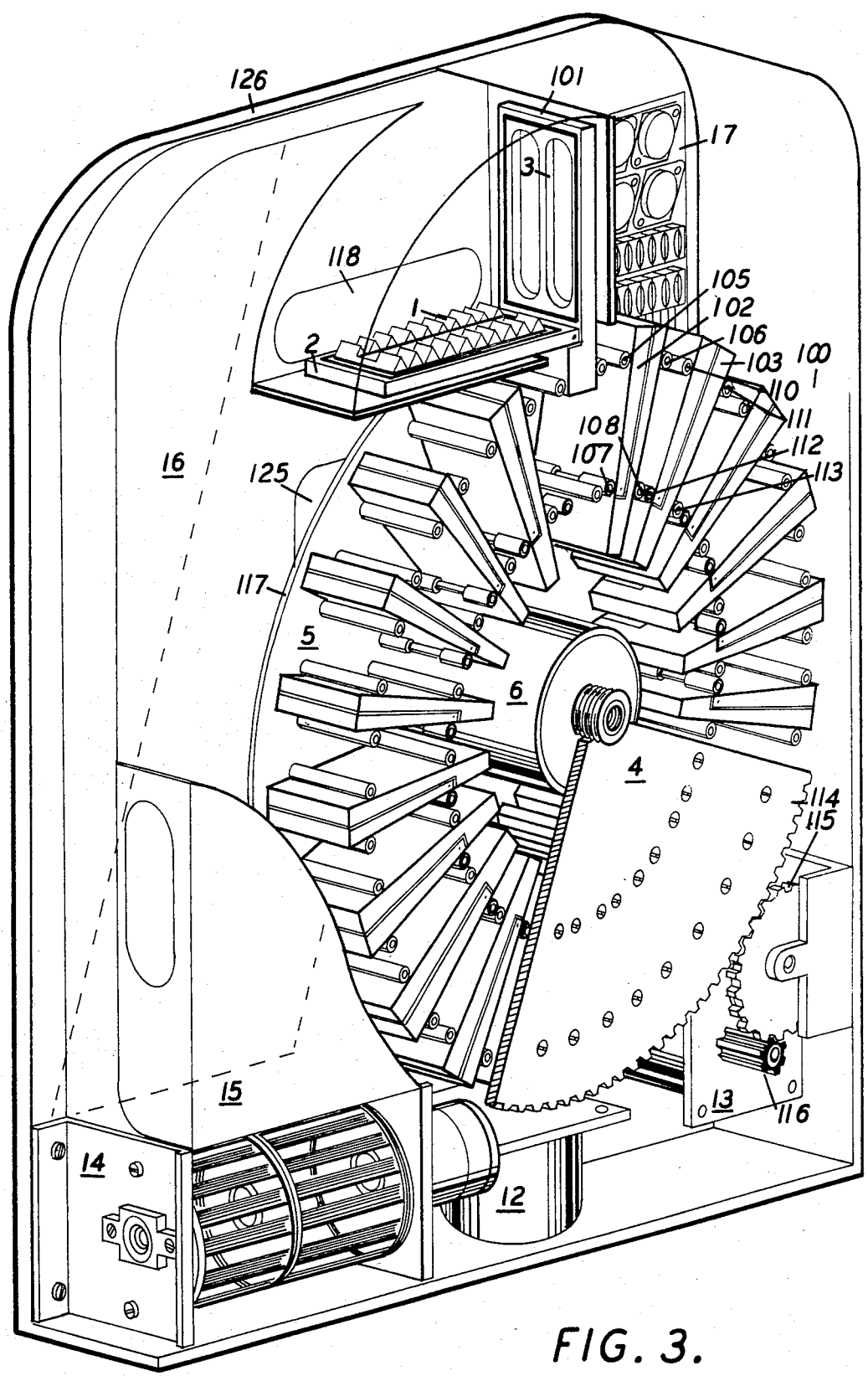
FIG. 3 is a perspective view of a preferred embodiment of the system with one scent-holding means open, and in operative relation with means for propelling scent released from the scent-holding means out of the system and toward a system user.
Figure 7:
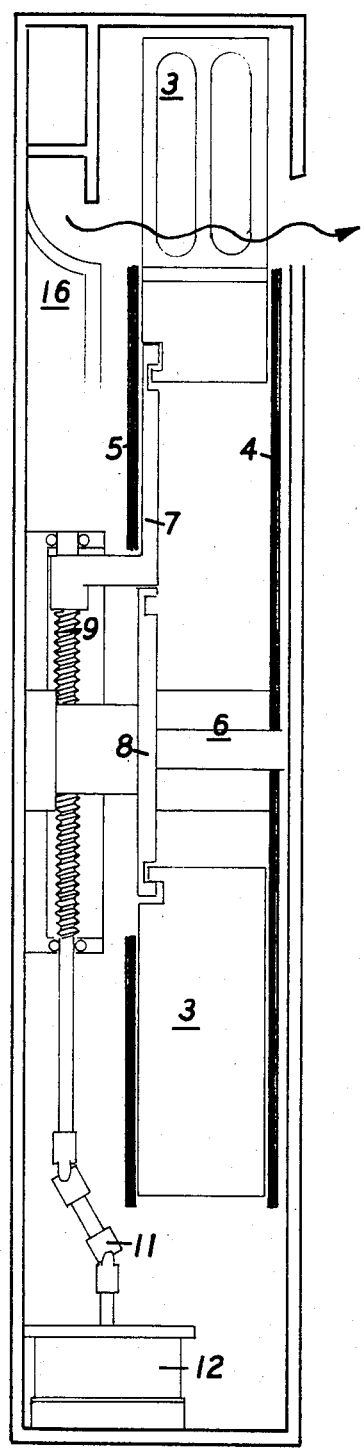
Figure 8:
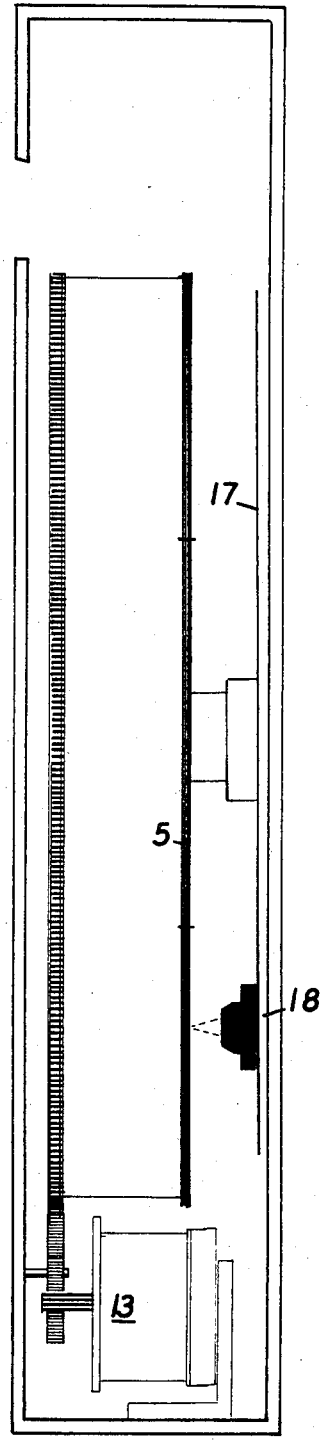
Figure 12:
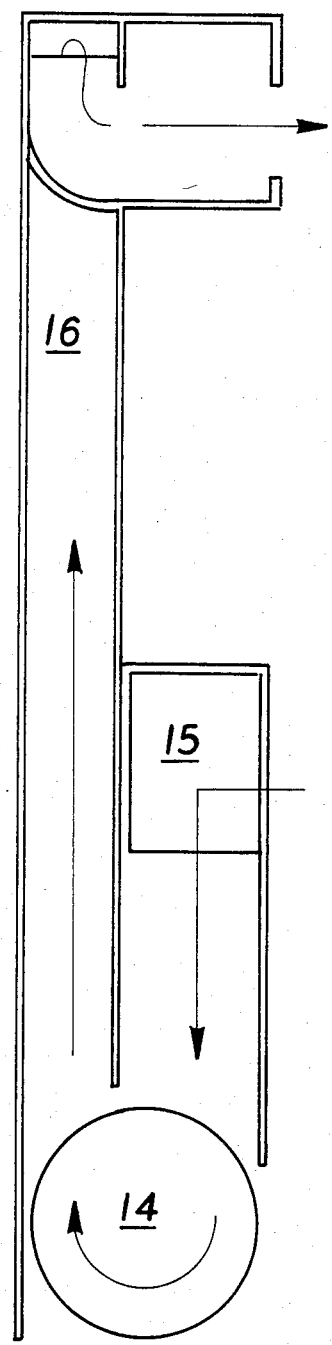
Figure 13:
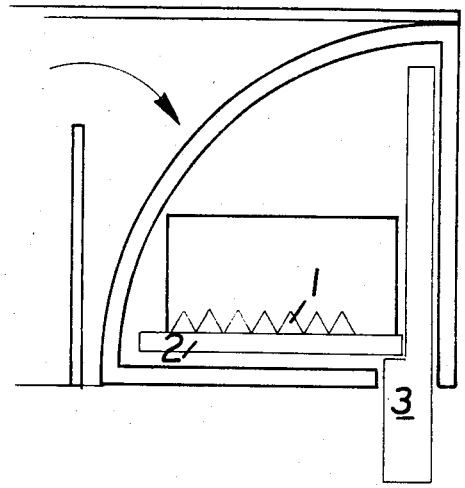
Figure 14:
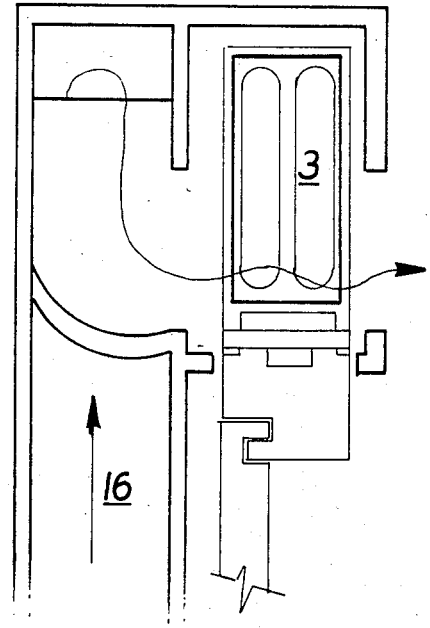
Figures 15, 15A, 15B:
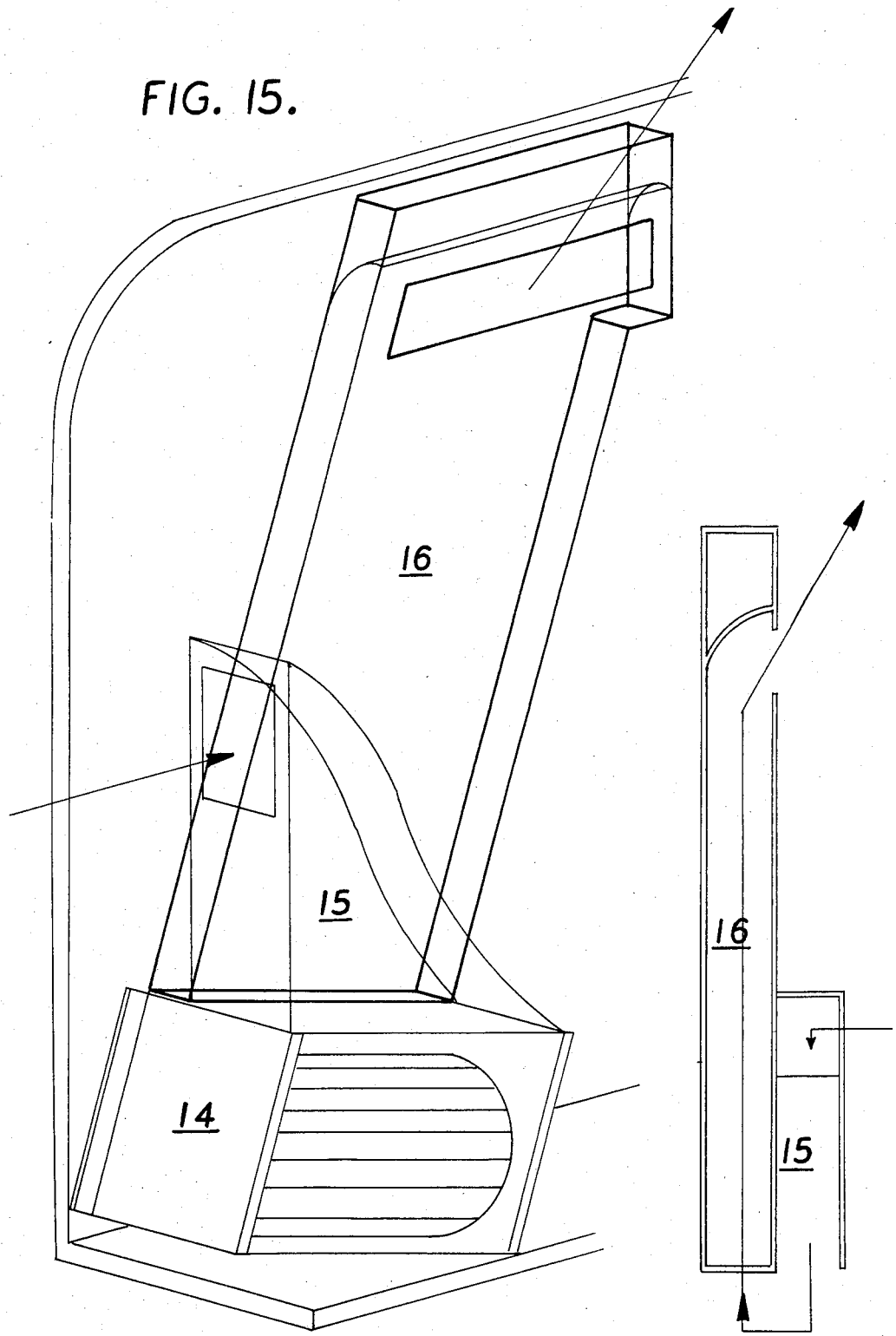
Figure 16:
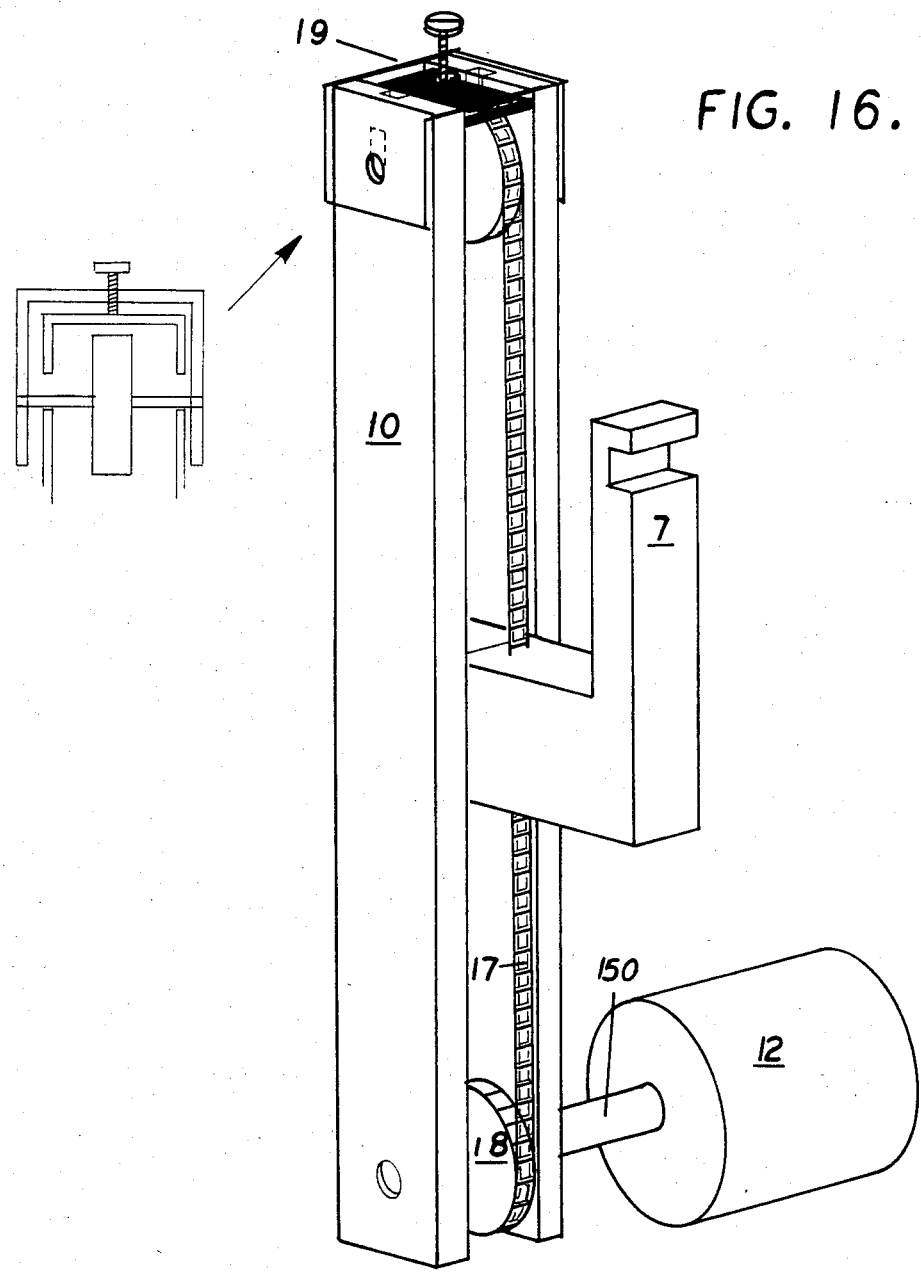
Figure 17:
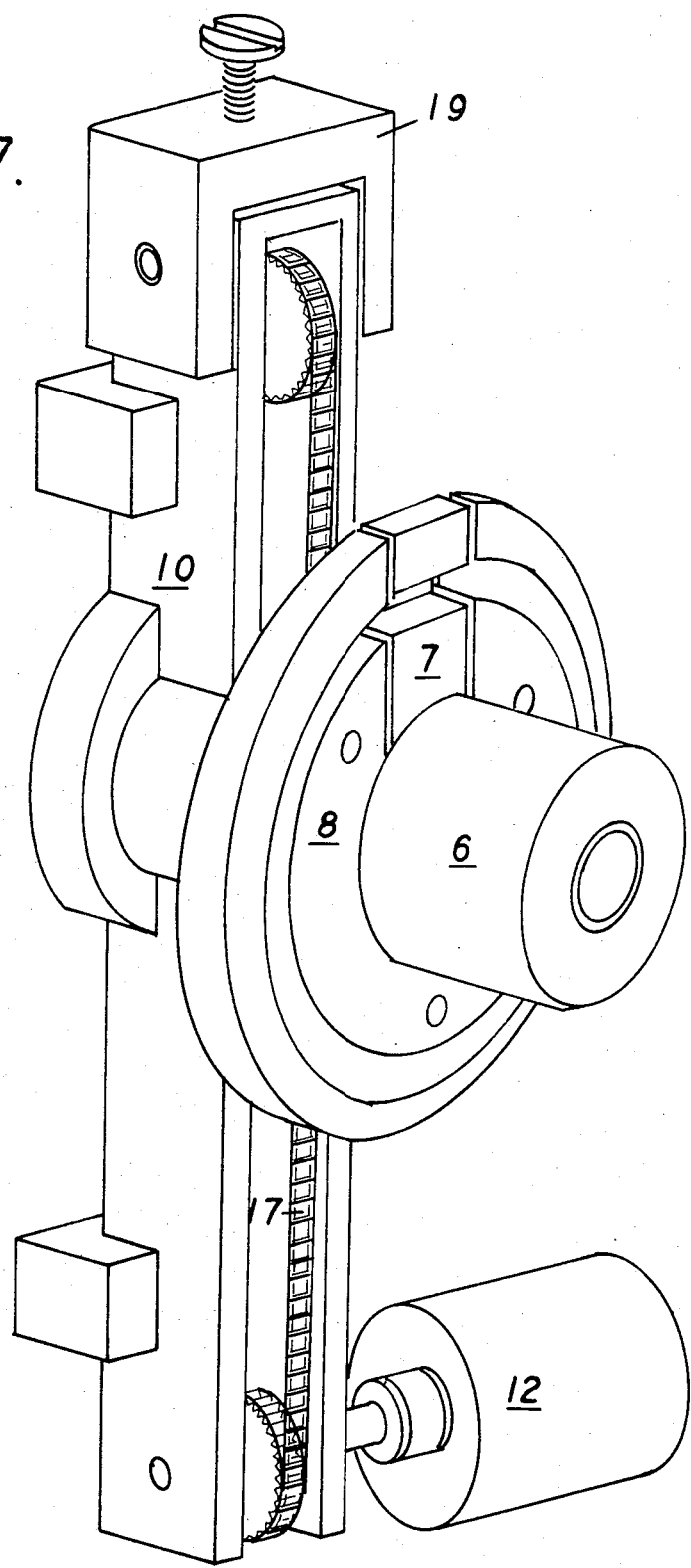

FIGS. 6B and 6C are exploded views of a portion of the embodiment shown in FIG. 3, here showing means for placing the scent-holding means (open for emission of scent confined within the holding means in FIG. 6C) in operative relation with, and for withdrawing the same scent-holding means from, operative relation with the scent-propelling means of the system, and for returning the scent-holding means to the closed position;

FIG. 7 is a sectional, end elevation view of the scent-emitting system embodiment illustrated in FIG. 3, taken on line 7—7 in FIG. 3;

FIG. 8 is another sectional end elevation view, taken on line 8—8 of FIG. 3, showing in part means for detecting the position of the rotatable means carrying the scent-holding means in relation to the scent-propelling means of the system embodiment in FIG. 3;

FIGS. 9A and 9B show, in exploded views, means for detecting the position of the rotatable means in relation to the scent-propelling means of the system embodiment in FIG. 3;

FIG. 10 is a block function diagram illustrating means for programming the system to emit one or more desired scents in desired sequence, at desired times and for desired durations;

FIG. 11 is a perspective view of the ducting that forms part of the propelling means of the system embodiment shown in FIG. 3;

FIG. 12 is an end elevation view of the duct means and blower means for drawing air or other gas into the propelling means of the system, and for directing the gas across the scent-bearing means to entrain and carry a desired scent;

FIGS. 13 and 14 show the flow of air or other gas over scent-bearing means for entrainment in the gas flow out of the system embodiment in FIG. 3;

FIGS. 15A and 15B illustrate an alternative embodiment of scent-propelling means for the new system including blower means and ducting means; and FIGS. 16 and 17 show an alternate embodiment of means for positioning a scent-holding means in operative relation with the scent-propelling means of the system.

FIG. 1 indicates that the new scent-emitting system carries to the olfactory nerves of a system user, in sequence, one or more desired scents, preferably in coordination with a film, picture or other representation of something or someone that emits the same scents. For example, the system can coordinate visual images of such objects as flowers, fruit or food with the smells of the flower, fruit or food depicted in the images.

FIG. 2 show that such coordination of sight and scent is useful in theaters where an embodiment of the scent-emitting system of this invention can be mounted on the back of each chair for emission of desired scents, in sequence, and for programmed, predetermined times, to persons seated in the path of scents flowing from the system.

As FIG. 2 indicates, a movie theater or a theater for live performances can have a plurality of scent-emitting systems, and preferably one for each theater-goer. The emission of scents from each unit in a theater can be coordinated so that all units emit the same scent, at the same time, and for the same duration. Moreover, the user of any one unit can turn off his unit entirely, or even vary the duration of emission of one or more of the scents programmed for emission.

FIG. 3 shows, in perspective view, a preferred embodiment of the scent-emitting system of this invention. In FIG. 3, the scent-holding means takes the form of a shell including rigid side 3, openable/closable side 2, and removable scent-emitting insert. Rotatable means, generally designated 100, includes a plurality of shell means such as 101, 102 and 103, each containing a scent-emitting chip. Shells 101, 102 and 103 are closed, and held in closed position by two roller pairs carried on rotatable means 100 between supporting members 4 and 5. For example, roller pairs 105/106 and 107/108 hold shell 102 closed as FIG. 3 shows. Similarly, roller pairs 109/110 and 111/112 hold shell means 103 closed. Members 4 and 5 are joined to each of the roller pairs, preventing them from moving out of proper alignment with shells 101, 102 and 103.

Side support 4 includes gear teeth 114 at its periphery that engage gear member 115. In turn, gear member 115 is driven by gear member 116 and wheel motor 13. Side member 5 includes, on its outer side 117, binary optical codes for indicating the position of rotatable means 100 in relation to exit means 118 of the system's scent-propelling means.

In FIG. 3, the scent-propelling means includes air intake 15, ductwork 16, blower and blower motor 14, and gas exit means 118. Air or other gas emerging from exit 118 passes over scent-emitting chip 1, entraining scent emitted from chip 1, and carrying the scent out of the system toward a system user.

FIG. 4 provides three views of one of the shell-like holding means for scent-bearing chip 1. Rigid side 3 of shell means 101 includes, at its periphery, resilient sealing means 119, which seats in complementary groove means 120 at the periphery of hinged shell side 2. The sealing action that results when sealing ring 119 seats in sealing groove 120 confines within shell means 101, when closed, scent emitted from scent-emitting chip 1. The irregular surface pattern of scent-emitting chip 1 increases the scent-emitting surface area of the chip. Hook 121 on shell 101 engages retaining means 122 (see FIGS. 5-7) to hold shell 101 on rotatable means 100, and to facilitate positioning shell 101 in operative relation with exit 118.

Figure 5:
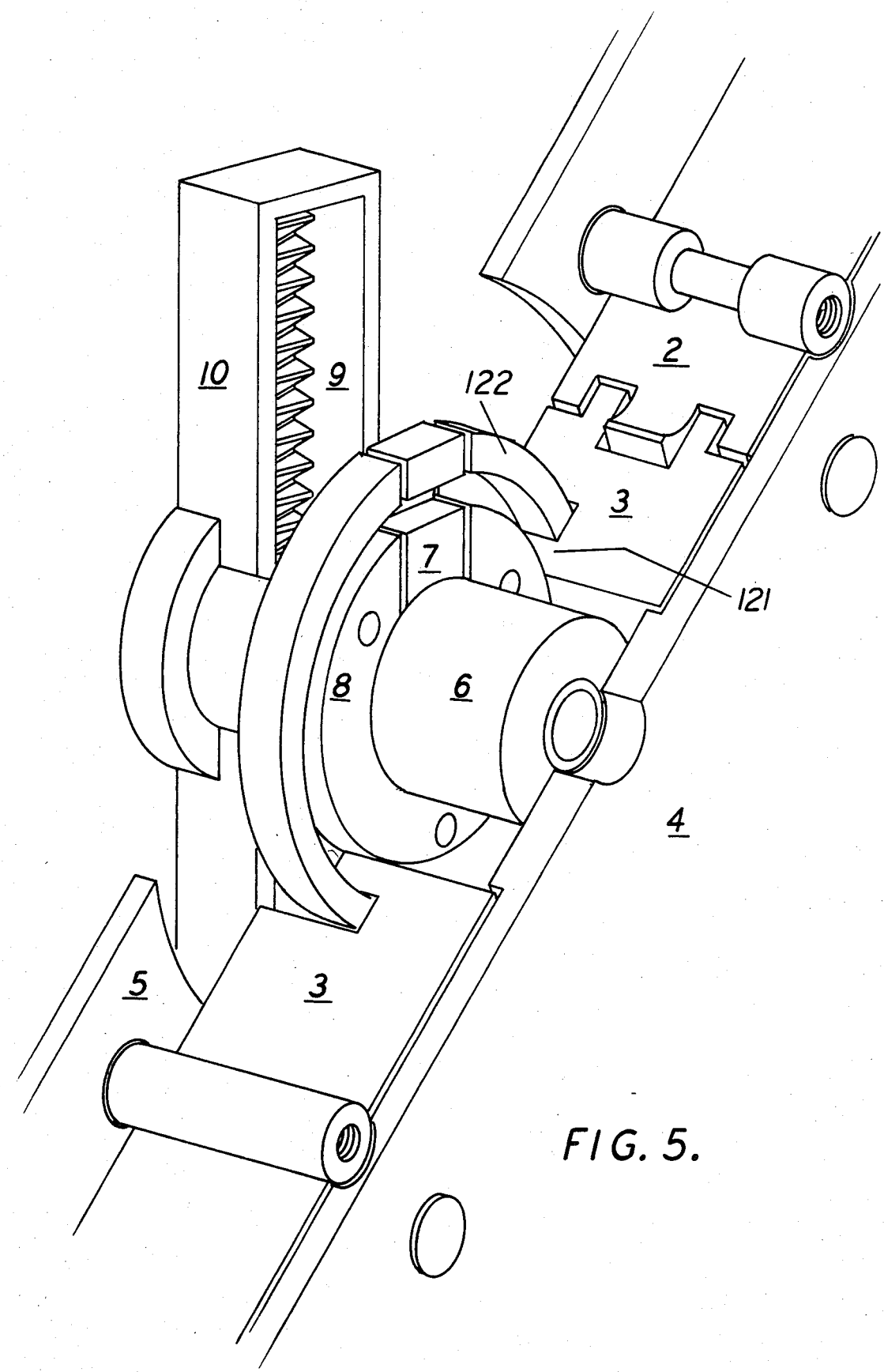
FIG. 5 shows an exploded detail view of the center portion of the system embodiment shown in FIG. 3.

FIG. 5 shows retaining means 122 in the form of a ring. Hook 121 at the bottom of shell 101 seats on, and engages retaining ring 122, but is free to move along retaining ring 122, as rotatable means 100 rotates about hub 6. FIGS. 6A, 6B and 6C show the operation of the means for positioning any desired shell, open for emission of scent confined within the shell, in operative relation with the scent-propelling means of the system. Rotatable means 100 carries the desired, selected shell 101 into engagement with shell positioning actuator 7, as FIG. 6B shows. Hook 3 at the bottom of shell 101 engages complementary hook 123 at the top of positioning actuator 7. Motor means 12 is actuated to rotate shaft 124 and drive screw 9, raising positioning actuator 7 and shell 101 to the position shown in FIGS. 3 and 6C. In this elevated position, hinged side 2 of shell 101 opens, permitting scent confined within shell 101 to be emitted. Emitted scent flows into the path of air emerging from exit 118. This emitted scent is entrained in the air, and carried from the system toward a system user.

FIGS. 8, 9A and 9B show that optical isolators 18 detect the position of rotatable means 100 by reading codes 19 carried on outer wall 124 of plate member 4. Optical isolators 18 are mounted on inner surface 125 of system cabinet 126 with their code-detecting means 127/128 facing outer wall 124.

FIG. 10 provides a block function diagram of means for programming the scent-emitting system of this invention to deliver desired scents in a desired sequence, at desired times, and for desired durations. The DATA IN block indicates input of a six-bit word dictating the desired scent, and the desired time for emission of that scent, from the system. Such inputs pass through an input data isolator 130, which prevents power surges from destroying the closest position memory, then to the closest position memory 131 on path 132. Memory 131 also receives signals on path 12 from binary position decoders 18 representing the position of the scent-holding means nearest to exit 118. From these data, memory 131 determines the shorter rotational distance that rotatable means 100 must travel to engage the desired scent-holding means with actuator 7.

Memory 131 then issues a signal on path 133 to motor drive memory 134, requiring actuation of main wheel motor 13 through path 135, motor driver 17 and path 136 to move rotatable means 100 in the desired direction and for the desired distance to engage the desired scent-holding means with actuator 7.

Motor drive memory 134 then issues a signal on path 135 to motor driver 17 to turn off main wheel motor 13, and to actuate motor 12. Motor drive memory 135 receives a signal from linear actuator position sensor 137 via path 138. When actuator 7 has raised the desired scent-holding means into position opposite exit 118, linear actuator position sensor 137 passes a signal to motor drive memory 134 via path 138, dictating issuance of a signal on path 135 to motor driver 17 and actuator motor 12, via path 139, to turn motor 12 off. Thereafter, motor drive memory 134 may issue a signal on path 135 to motor driver 17 to turn on, or to accelerate motor 14 to propel scent from the system.

FIG. 11 shows in greater detail the flow of air through the ductwork in the scent-propelling means of the system. Air enters the ductwork through intake 141, and travels along the path indicated by the arrows and lines upwardly through ductwork 16, into funnel 142, and emerges from the ductwork through exit 118.

As better seen in FIGS. 12-14, blower 14 propels air through ductwork 16 at a rate proportional to the speed of blower 14, and then out, across and through scent-bearing chip 1.

FIGS. 15A and 15B show an alternate ductwork arrangement for a system that is smaller in size than the system illustrated in FIGS. 1-14.

FIGS. 16 and 17 show an alternate embodiment for raising and lowering actuator 7. In FIGS. 16 and 17, linear actuator 7 is carried on chain 17. Chain 17 is driven by gear 18 linked to motor 12 through shaft 150. Tension adjuster 19 permits adjustment of the tension in chain 17, as necessary or desirable.

What is claimed is:

1. A method for sequentially directing at least two different scents from a gaseous scent-emitting system toward at least one and no more than about five persons comprising selecting for emission the desired scents from said plurality of different gaseous scents; generating a signal representing the selected, desired scents; sequentially conveying solid, scent-bearing emitters of the selected, desired gaseous scents, carried on rotatable means having a plurality of said emitters therein, to scent-propelling means withing said system in response to said signal; opening said selected emitters in any desired sequence at said scent-propelling means and directly opposite exit means in said system for said gaseous scent to release the selected, desired scent; and propelling the released gaseous scents desired, in sequence, from said system through said exit means toward said at least one, but no more than about five persons.

2. A system for sequentially emitting at least one of a plurality of different scents comprising a plurality of means for holding solid scent-bearing, gaseous scent-emitting means; exit means from said system; rotatable means carrying said plurality of holding means within said system toward and away from said exit means; means for propelling said scent in gaseous form from said system through said exit means, said propelling means comprising means for blowing a gas over the scent-bearing, gaseous scent-emitting means and for directing gas-entrained gaseous scent directly through said exit means; means for selectively conveying any desired holding means carried on said rotatable means into operative relation with said propelling means, and adjacent to said exit means; and means for actuating said propelling means to propel gaseous scent entrained in said gas from said desired holding means.

3. The system of claim 2 wherein each of said holding means is an openable, closable shell that opens to release scent confined within said shell when said shell is in operative relation with said propelling means.

4. The system of claim 3 further comprising means for inputting a signal representing a desired scent and the time for emitting the desired scent; means for generating a signal representing the position of the rotatable means carrying the scent-bearing means into operative relation with the scent-propelling means; means for generating a signal representing the necessary distance and direction of rotation of the rotatable means to engage the desired scent-bearing means with means for positioning said scent-bearing means in operative relation with the scent-propelling means; means for generating a signal to place the desired scent-bearing means into operative relation with the propelling means and to open the scent-bearing means to emit the desired scent; and means for actuating means for propelling a gas across the exposed scent-bearing means to entrain and carry the desired scent through the system exit toward one or more persons.

5. The system of claim 3 wherein said scent-bearing means is a replaceable, scent-impregnated, gaseous scent-emitting insert means for said shell.

6. The system of claim 5 wherein said conveying means comprises means for carrying said desired holding means toward and away from said propelling means, and means for opening said desired holding means to release gaseous scent emitted from scent-bearing means and confined within said holding means directly opposite said exit means.

7. The system of claim 5 further comprising means for inputting a signal representing a desired scent and the time for emitting the desired scent; means for generating a signal representing the position of the rotatable means carrying the scent-bearing means into operative relation with the scent-propelling means; means for generating a signal representing the necessary distance and direction of rotation of the rotatable means to engage the desired scent-bearing means with means for positioning said scent-bearing means in operative relation with the scent-propelling means; means for generating a signal to place the desired scent-bearing means into operative relation with the propelling means and to open the scent-bearing means to emit the desired scent; and means for actuating means for propelling a gas across the exposed scent-bearing means to entrain and carry the desired scent through the system exit toward one or more persons.

8. The system of claim 1 wherein said gas is air.

9. The system of claim 2 further comprising means for inputting a signal representing a desired scent and the time for emitting the desired scent; means for generating a signal representing the position of the rotatable means carrying the scent-bearing means into operative relation with the scent-propelling means; means for generating a signal representing the necessary distance and direction of rotation of the rotatable means to engage the desired scent-bearing means with means for positioning said scent-bearing means in operative relation with the scent-propelling means; means for generating a signal to place the desired scent-bearing means into operative relation with the propelling means and to open the scent-bearing means to emit the desired scent; and means for actuating means for propelling a gas across the exposed scent-bearing means to entrain and carry the desired scent through the system exit toward one or more persons.

10. A system for sequentially emitting at least two different gaseous scents entrained in air comprising exit means from said system; rotatable means for carrying, toward and away from said exit means, a plurality of shell means for holding solid scent-bearing, gaseous scent-emitting means and for confining gaseous scent emitted from said scent-bearing, gaseous scent-emitting means; means for propelling said gaseous scents from said system entrained in air through said exit means directly opposite said propelling means; means for selectively conveying any desired shell means into operative relation with said propelling means and with said exit means, including means for opening said desired shell means to release gaseous scent emitted from a replaceable, scent-impregnated, gaseous scent-emitting insert means confined within said desired shell means; and means for actuating said propelling means to propel said gaseous scent from said desired shell means, entrained in air, directly through said exit means.

11. The system of claim 10 further comprising means for generating a signal representative of said desired shell means, and means for utilizing said signal to actuate said rotatable means and said positioning means.

12. The system of claim 11 further comprising means for inputting a signal representing a desired scent and the time for emitting the desired scent; means for generating a signal representing the position of the rotatable means carrying the scent-bearing means into operative relation with the scent-propelling means; means for generating a signal representing the necessary distance and direction of rotation of the rotatable means to engage the desired scent-bearing means with means for positioning said scent-bearing means in operative relation with the scent-propelling means; means for generating a signal to place the desired scent-bearing means into operative relation with the propelling means and to open the scent-bearing means to emit the desired scent; and means for actuating means for propelling a gas across the exposed scent-bearing means to entrain and carry the desired scent through the system exit toward one or more persons.

13. The system of claim 10 further comprising means for inputting a signal representing a desired scent and the time for emitting the desired scent; means for generating a signal representing the position of the rotatable means carrying the scent-bearing means into operative relation with the scent-propelling means; means for generating a signal representing the necessary distance and direction of rotation of the rotatable means to engage the desired scent-bearing means with means for positioning said scent-bearing means in operative relation with the scent-propelling means; means for generating a signal to place the desired scent-bearing means into operative relation with the propelling means and to open the scent-bearing means to emit the desired scent; and means for actuating means for propelling a gas across the exposed scent-bearing means to entrain and carry the desired scent through the system exit toward one or more persons.

* * * * *